United States Patent [19]

Clegg et al.

[11] Patent Number: 5,057,093
[45] Date of Patent: Oct. 15, 1991

[54] MEDICAL DEVICE IMPROVEMENTS FOR ENTERAL FEEDING

[75] Inventors: Robert D. Clegg, Pickerington, Ohio; Ronald A. Coules, Barrington, Ill.; Kent E. Iversen, Columbus; Robert S. Osborne, Gahanna, both of Ohio; Patricia A. Schneider, Wauconda, Ill.

[73] Assignee: Abbott Laboratories, Abbott Park, Ill.

[21] Appl. No.: 404,940

[22] Filed: Sep. 7, 1989

[51] Int. Cl.⁵ .............................................. A61M 3/00
[52] U.S. Cl. .................................... 604/283; 604/256; 604/905; 128/912
[58] Field of Search ............... 604/283, 284, 905, 256, 604/282, 326; 285/332, 177, 12, 320; 128/912

[56] References Cited

U.S. PATENT DOCUMENTS

| | | | |
|---|---|---|---|
| 2,763,266 | 9/1956 | Evans | 604/283 |
| 3,513,849 | 5/1970 | Vaillancourt et al. | 604/283 |
| 3,731,684 | 5/1973 | Spiegel | 604/256 |
| 3,741,217 | 6/1973 | Ciarico | 604/256 |
| 3,835,862 | 9/1974 | Villari | 604/283 |
| 4,013,080 | 3/1977 | Froning | 604/165 |
| 4,045,058 | 8/1977 | Eross | 604/283 |
| 4,230,345 | 10/1980 | Boelkins | 285/320 |
| 4,326,516 | 4/1982 | Schultz et al. | 604/283 |
| 4,349,024 | 9/1982 | Ralston, Jr. | 604/905 |
| 4,731,061 | 3/1988 | Matkovich | 604/256 |

FOREIGN PATENT DOCUMENTS

| | | | |
|---|---|---|---|
| 1491988 | 8/1967 | France | 285/177 |
| 1199498 | 7/1970 | United Kingdom | 604/256 |

*Primary Examiner*—Stephen C. Pellegrino
*Assistant Examiner*—Ralph A. Lewis
*Attorney, Agent, or Firm*—Lonnie R. Drayer; Donald O. Nickey; E. H. Gorman, Jr.

[57] ABSTRACT

Improved medical devices for use between a feeding tube set and a catheter include a universal adaptor having a configuration permitting use of same with Y-connectors of various sizes, a Y-connector interlockable with the aforesaid adaptor, and an adaptor hood usable with the adaptor either as a protective shroud therefor or as a supplemental adaptor therewith.

14 Claims, 3 Drawing Sheets

MEDICAL DEVICE IMPROVEMENTS FOR ENTERAL FEEDING

TECHNICAL FIELD

The present invention relates to medical devices which are used between a feeding tube set which is connected to a supply or source of a liquid medical nutritional product and the proximal end of a feeding catheter (either nasogastric or gastrostomic) which has been suitably positioned in a patient's gastro/intestinal tract.

BACKGROUND OF THE INVENTION

When a patient is in need of enteral feeding, a feeding catheter is placed into the patient either percutaneously or via a nosogastric tube. The feeding catheter is then connected to a source of nutrition which usually comprises a container holding the liquid nutritional product and tubing (feeding tube set). Different size adaptors are normally provided at the distal end of the feeding tube set for interfitting frictional engagement with the feeding catheter. Further, for many obvious reasons, such frictionally engaged connections may inadvertently become disengaged or separated which, of course, could be detrimental to varying degrees, to the patient's well-being.

After fabrication and until such time that they are connected to a patient's feeding catheter, such adaptors provided on the distal end of a feeding tube set, are often provided with a protective hood or shroud of an appropriate size having a closed forward end and whose only purpose is to protect the adaptor until use of same.

Adaptors currently in the market place, while compatible with most nasogastric, gastrostomic and I.V. feeding tube connectors currently found in the marketplace, are not compatible with the relatively small "needle jejunostomy" catheters. The needle jajunostomy catheter is characterized by relatively small connectors having luer-tapered bores which are not adapted to receive the leading ends of most adaptors. To date, the only solution has been to provide a special custom-designed adaptor, a rather expensive solution to this problem.

DISCLOSURE OF THE INVENTION

In general the present invention relates to an improved medical device comprising an adaptor for use between a feeding tube and a catheter, the improved medical device comprising a tubular adaptor mountable on the distal end of a feeding tube and having progressively smaller diameter stepped surfaces on the outer surface thereof from the feeding tube end thereof to the opposite end thereof and with said outer surface configuration optionally including an inverted conical section, a tubular connector mountable on the proximal end of a catheter and having at the opposite end thereof an adaptor-receiving port of any one of several diameters, any one of which ports will insertably receive said adaptor, releasable positive interlock means engageable between said adaptor and said connector when same are assembled together, and a tubular hood having a tip with a luer taper and fittable over said adaptor to serve either as a protective shroud or as a supplemental adaptor for use with connectors wherein said adaptor-receiving port thereof is provided with an internal luer taper.

There is disclosed a device which comprises an adaptor, a connector and an adaptor hood for use in various combinations between a feeding tube set and a feeding catheter;

said adaptor comprising a first generally tubular member having an upper end adapted to be mounted on the distal end of a feeding tube and a lower end adapted to be inserted into the upper end of either said connector or into said adaptor hood, the outer surface of said adaptor being characterized by a series of steps of progressively smaller diameters from the upper to the lower end thereof and including at least one inverted, slightly conical section, and a ring member projecting radially from said upper end of said tubular member in a longitudinal plane and adapted to have a locking plug of said connector removably secured therein;

said connector comprising a second generally tubular member mounted on the proximal end of a catheter and having an open end with any one of a plurality of inner diameters and adapted to receive therein the stepped lower end of said adaptor, a locking plug projecting radially from the upper portion of said tubular member on a flexible, resilient arm with said plug being adapted either for plugging said open upper end of said tubular member when no adaptor is received therein or for being lockingly engaged in said adaptor ring member when said adaptor is received in said open upper end of said connector to prevent inadvertent separation of said adaptor and said connector; and said adaptor hood comprising a third generally tubular member having an open upper end, an inner bore which tapers inwardly in a downward direction, and a tip at its lower end with the outer surface thereof being provided with a luer taper for interfitting engagement thereof in the open upper end of a connector having a bore with a luer taper, which connector is mounted on the proximal end of a catheter.

There is also disclosed a device which comprises an adaptor and a connector for use in combination between a feeding tube set and a catheter;

said adaptor comprising a first generally tubular member having an upper end adapted to be mounted on the distal end of a feeding tube and a lower end adapted to be inserted into the upper end of said connector, the outer surface of said adaptor being characterized by a series of steps of progressively smaller diameters from the upper to the lower end thereof and including at least one inverted, slightly conical section, and a ring member projecting radially from said upper end of said tubular member in a longitudinal plane and adapted to have a locking plug of said connector removably secured therein; and said connector comprising a second generally tubular member mounted on the proximal end of a catheter and having an open end with any one of a plurality of inner diameters and adapted to receive therein the stepped lower end of said adaptor, a locking plug projecting radially from the upper portion of said tubular member on a flexible, resilient arm with said plug being adapted either for plugging said open upper end of said tubular member when no adaptor is received in said open upper end of said connector to prevent inadvertent separation of said adaptor and said connector.

There is further disclosed an adaptor and adaptor hood for use in combination between a feeding tube set and a catheter;

said adaptor comprising a first generally tubular member having an upper end adapted to be mounted on the distal end of a feeding tube and a lower end adapted to be inserted into said adaptor hood, the outer surface of said adaptor being characterized by a series of steps of progressively smaller diameters from the upper to the lower end thereof and including at least one inverted, slightly conical section, and a ring member projecting radially from said upper end of said tubular member in a longitudinal plane; and said adaptor hood comprising a second generally tubular member having an open upper end, and inner bore which tapers inwardly in a downward direction, and a tip at its lower end with the outer surface thereof being provided with a luer taper, said second tubular member being adapted to be fitted over said first tubular member from the lower end thereof for either providing a protective cover for said adaptor during transport or storage thereof or for providing interfitting engagement thereof in the open upper end of a connector mounted on the proximal end of a catheter, which open upper end is characterized by a bore having a luer taper.

There is disclosed for use between a feeding tube set and a catheter connector; an adaptor comprising a generally tubular member having an upper end adapted to be mounted on the distal end of a feeding tube and a lower end adapted to be inserted into the upper end of said catheter connector, and a locking ring member projecting radially from said upper end of said tubular member in a longitudinal plane for interlocking engagement by a locking plug on said catheter connecter.

There is also disclosed for use between an adaptor of a feeding tube set and a catheter, a connector comprising a generally tubular member mounted on the proximal end of a catheter and having an open end adapted to receive said feeding tube adaptor therein; a locking plug projecting radially from the upper portion of said tubular member on a flexible, resilient arm for interlocking engagement with said feeding tube adaptor to prevent inadvertent separation of said connector from said adaptor.

There is further disclosed for use with an adaptor of a feeding tube set; an adaptor hood comprising a generally tubular member having an open upper end, a through bore which tapers inwardly in a downward direction from said open upper end, and a tip at its lower end with the outer surface thereof being provided with a luer taper, said tubular member being adapted to be fitted over a tubular adaptor of a feeding tube set from the lower end thereof for either providing a protective cover for said adaptor during transport or storage of the feeding tube set or for interfitting engagement thereof in the open upper end of a catheter connector having a bore with a luer taper.

There is also disclosed for use between a feeding tube and a catheter, a positive interlock comprising a generally tubular connector mounted at the proximal end of a catheter and having an adaptor-receiving entrance port provided at its other end; a generally tubular adaptor having one end mounted on the distal end of a feeding tube and its other end insertable into said adaptor-receiving entrance port of said connector; a ring formation on said adaptor; and a plug member secured to said connector by a flexible arm and releasably engageable through said adaptor ring formation.

The present invention, in general, relates to improvements in specialized medical devices, specifically improvements in the adaptors, connectors and hoods, which overcomes the problems discussed herein. One improvement is to provide an adaptor design of one size which can be used with connectors of various sizes. The outer adaptor surface has a new and novel arrangement of step portions of progressively increasing diameters (from the tip thereof) in combination with a conical portion. As a result of this single improvement, a major economical advantage results from the need to fabricate only a single size adaptor and protective hood therefor.

Another improvement is the provision of a new and novel adaptor hood having a forward end or tip which is open to permit a fluid flow there through and which is provided with an external luer taper adapted for interfitting engagement in the luer-tapered bore of the previously noted "needle jejunostomy" catheters. If a feeding tube set provided with the unique adaptor and the unique protective adaptor hood of the subject invention is to be used in conjunction with one of the aforesaid "needle jejunostomy" catheters, the hood which is frictionally press-fitted over the adaptor is retained thereon and the luer-tapered tip of the hood is frictionally received in the luer-tapered bore of the catheter connector to provide a perfectly adequate feeding arrangement.

Still another improvement is the arrangement of interlocking means between the new and novel adaptor of the present invention and the catheter connector which prevents inadvertent separation of same during feeding of a patient. A preferred form of interlocking means is the provision of a ring on the adaptor which is adapted to lockingly receive there through the plug provided on the end of a flexible arm secured to or integral with many connectors and normally intended for use in plugging the main port of the connector when an adaptor of a feeding tube set is not engaged therein.

Therefore, one aspect of the present invention is to provide improvements in medical devices used in the fluid-feeding of patients through plastic tubing, specifically adaptors, connectors and adaptor hoods.

Another aspect of the present invention is to provide a universal adaptor of new and novel external configuration for use with catheter connectors of various sizes.

A further aspect of the present invention resides in the adaptor hood which may be used not only as a protective shroud for the adaptor disclosed herein, but also as an auxiliary adaptor for use with extremely small catheter connectors having luer-tapered bores.

An additional aspect of the present invention provides interlocking means between the feeding tube connector and the adaptor disclosed herein which will prevent or reduce the inadvertent separation thereof during a patient-feeding procedure.

BRIEF DESCRIPTION OF THE DRAWINGS

FIG. 1 shows an adaptor and an adaptor hood embodying the invention prior to the hood being fitted over the adaptor, no pumping means being shown in this view.

DESCRIPTION OF PREFERRED EMBODIMENTS

Figures 1, 2, 3:
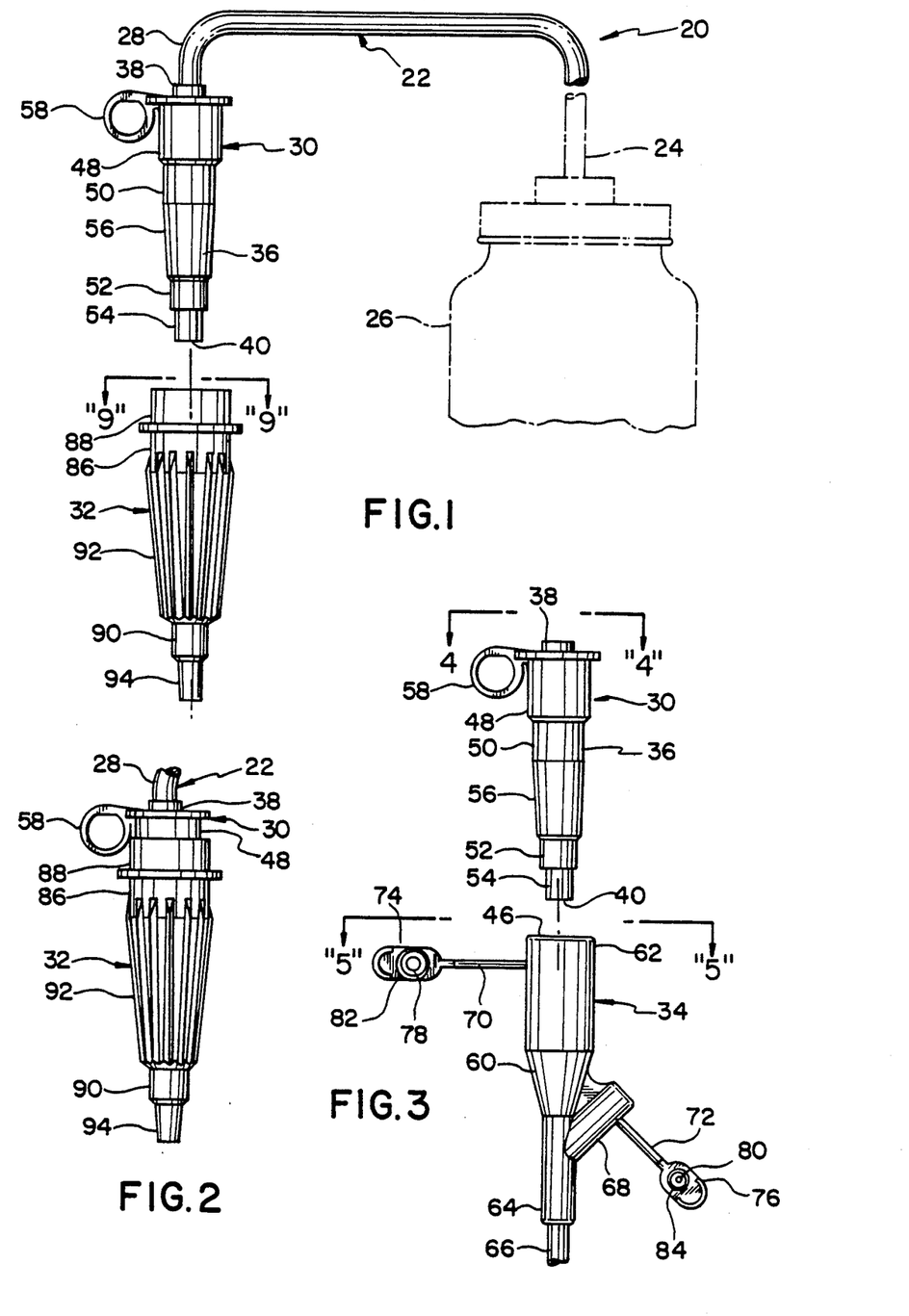
FIG. 1 is a side elevational view of portions of a feeding tube set with the fluid nutrient supply shown partially in broken lines.
FIG. 2 is a side elevational view of the assembled adaptor and adaptor hood of FIG. 1.
FIG. 3 is a side elevational view of the adaptor of FIG. 1 prior to insertion of same into a feeding catheter Y-connector.

Referring now to the drawings, the feeding tube set 20 partially shown in FIG. 1 includes a plastic feeding tube 22 having its proximal end 24 connected to a supply jar 26 of fluid nutrient and its distal end 28 secured in the entrance end of a new and novel adaptor 30 embodying a portion of the present invention. As the supply jar or container 26 is not illustrated in a gravity-feed mode, the feeding tube set 20 would also include a known-type pumping means (not shown). The present invention as it relates to the hood is shown in FIG. 1 prior to its being fitted over the adaptor 30 to serve as a protective shroud during storage and transport of the feeding tube set 20 and in FIG. 2 after fitting of same over the adaptor 30. In FIG. 3, the adaptor 30 is shown prior to insertion of same into a new and novel connector 34 which also embodies a portion of the present invention. These three new and novel medical devices 30, 32 and 34 interact and interconnect as shown in the drawings and will be further described hereinafter to illustrate the several improvements and economic savings in the delivery of liquid nutrients to patients.

Figure 4:
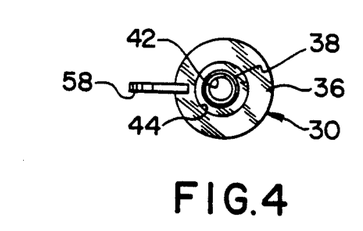
FIG. 4 is a top plan view of the adaptor taken generally along line 4—4 of FIG. 3.
Figure 10:
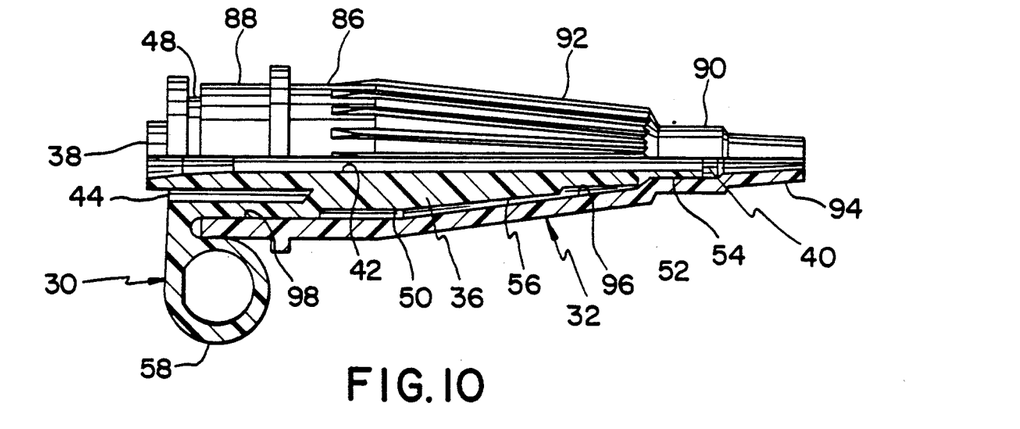
FIG. 10 is an enlarged view of the assembled adaptor and adaptor hood with the portion above the longitudinal axis thereof being shown in elevation and the portion below the longitudinal axis thereof being shown in vertical section.

As best illustrated in FIGS. 3, 4, and 10, the adaptor 30 is characterized by a generally tubular body portion 36 molded of a suitable plastic and having a larger diameter entrance or upper end 38 as viewed in FIG. 3, and a smaller diameter exit or lower end 40. An axial bore 42 extends through the body portion 36. An annular coaxial slot 44 is provided in the larger diameter end 38, as shown in the sectional portion of FIG. 10, whereby the adaptor 30 may be fixedly mounted either on the distal end of a larger diameter feeding tube 22 with the end of the tube 22 being received in the annular slot 44 or on the distal end of a smaller diameter feeding tube 22 with the end of the tube 22 being fixedly received in the adjacent end of the bore 42 (see FIGS. 1, 2, 6, 8 and 11). The exit end 40 of the adaptor 30 is adapted to be removably inserted into a main entrance port 46 of any one of several connectors 34 of various sizes, as shown, for example, in FIGS. 6 and 8, the entrance ports 46 of such connectors 34 also varying in size. So that custom-sized adaptors need not be provided for each size connector 34, the new and novel adaptor 30 of the present invention is provided with an outer surface which is characterized by a series of step surfaces 48, 50, 52 and 54 of progressively smaller diameters from the entrance end 38 of the adaptor 30 to the exit end 40 thereof with an inverted, slightly conical section 56 being disposed between the step surfaces 50 and 52.

Figure 6:
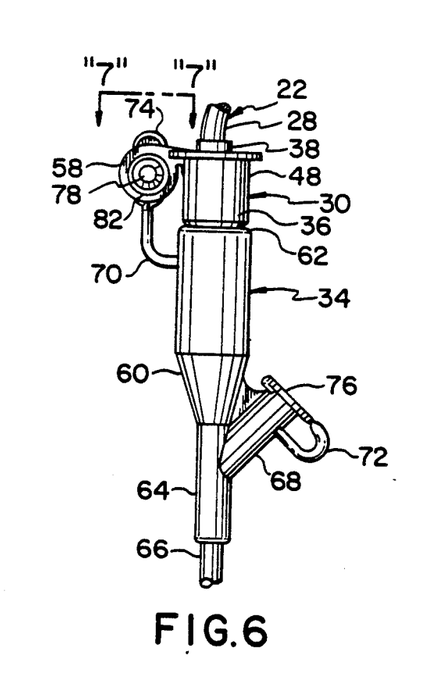
FIG. 6 is a side elevational view of the adaptor of FIGS. 1 and 3 assembled in a relatively large catheter Y-connector and showing the interlocking means engaged and the smaller Y-arm plug inserted in the side port.
Figure 8:
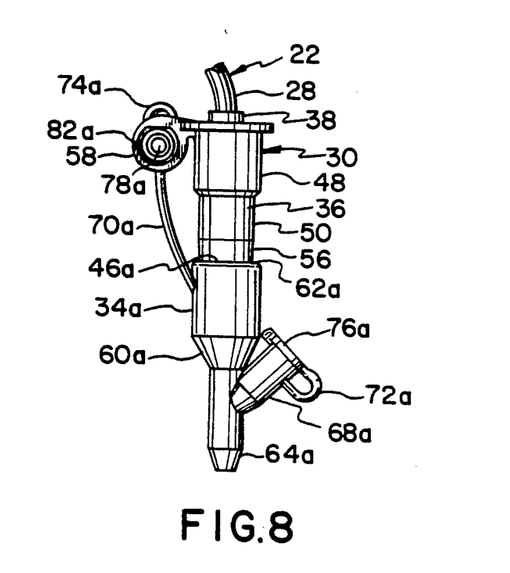
FIG. 8 is a side elevational view similar to FIG. 6 but showing the adaptor of FIGS. 1 and 3 assembled in a relatively small catheter Y-connector and also showing the interlocking means engaged and the smaller Y-arm plug.

The practical application and advantages of this universal adaptor configuration are illustrated by a comparison of FIGS. 6 and 8. In FIG. 6, the adaptor 30 is shown inserted into a larger size connector 34 with the second largest stop surface 50 being snuggly received in the main entrance port 46 of the connector 34. In FIG. 8, with a much smaller connector 34a, the conical section 56 of the same adaptor 30 is snuggly received in the main entrance port 46a of the connector 34a.

As will be discussed more fully hereinafter, the adaptor 30 is provided at the outer edge of its entrance end 38 with an integral longitudinally disposed and radially extending locking ring 58.

Figure 5:
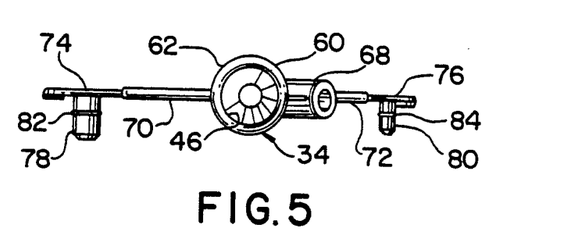
FIG. 5 is a top plan view of the Y-connector taken generally along line 5—5 of FIG. 3.

The Y-connector 34, as best shown in FIGS. 3, 5 and 6, is characterized by a generally tubular body member 60 molded of a suitable plastic with a larger diameter entrance or upper (as viewed in the aforesaid FIGS.) end 62 in which the main entrance port 46 is provided and a smaller diameter exit or lower end 64 which is secured on the proximal end of a catheter 66 (FIGS. 3 and 6). A secondary port for the administration of a medicament during a feeding operation is provided in a secondary smaller tubular arm 68 which intersects the main bore through the tubular body member at an angle. Both the upper end 62 and the secondary arm 68 are provided with radially extending flexible arms 70 and 72, respectively, with enlarged end formations 74 and 76, respectively, provided thereon. The end formation 74 is provided with a plug formation 78 of a size to be snuggly received within the main entrance port 46 when no adaptor 30 is inserted therein. A smaller plug formation 80 is provided on the end formation 76 of a size to be snuggly received within the port in the secondary arm 68 when no medicament is being introduced therein. Each plug formation 78 and 80 is provided with a compressible annular ring 82 and 84, respectively, for latching engagement in annular grooves (not shown) provided in the main entrance port 46 and the port of the secondary arm 68. As is shown in FIG. 8, the smaller connector 34a is likewise characterized by a flexible arm 70a, a plug formation 78a, and the like.

Figure 7:
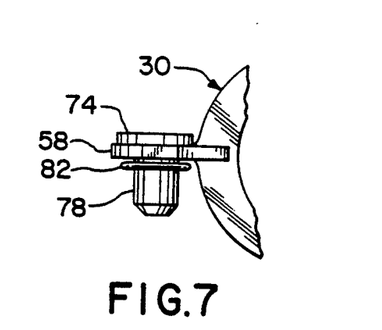
FIG. 7 is an enlarged partial top plan view of the engaged adaptor connector interlocking means taken generally along line 7—7 of FIG. 6.

As previously noted herein, one problem with most adaptor/connector assemblies is the possibility of separation during feeding of the patient. With the new and novel adaptor 30 and the Y-connector 34 disclosed herein, this problem has been minimized by providing a positive interlock between the adaptor 30 and its associated connectors 34 and 34a. As illustrated in FIGS. 6, 7 and 8, the plug formations 78 and 78a of the Y-connectors 34 and 34a of FIGS. 6 and 8, respectively, are removably engageable in the locking ring 58 of the adaptor 30. As best illustrated in FIG. 7, the compressible annular rings 82 and 82a on the plug formations 78 and 78a are easily forced through the locking ring 58 so that they are engageable with the surfaces opposite the surfaces engaged by the enlarged end formations 74 and 74a of the connectors 34 and 34a, respectively, whereby to provide a positive interlocking relationship between the adaptors 30 and their assembled connectors 34 and 34a.

Although, as in FIG. 6, there need not be any tension in the flexible arm 70 when the plug formation 78 thereon is interlocked with the adaptor locking ring 58, it is sometimes preferable, as in FIG. 8, that the flexible arm 70a be under slight tension when its plug formation 78a is so interlocked in the adaptor locking ring 58 to minimize any loosening of the assembly of the adaptor 30 in the Y-connector 34a.

Figure 11:
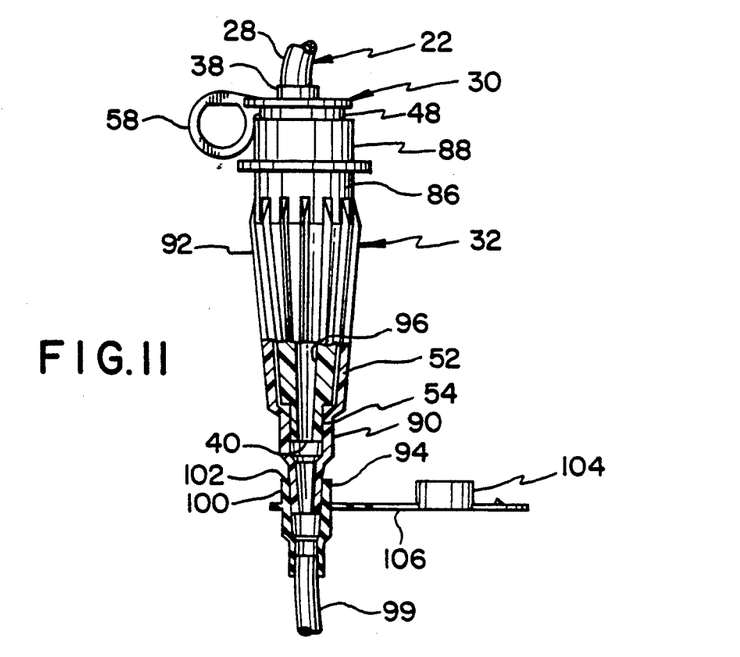
FIG. 11 is a side elevational view, with the lower portion being shown in section, of the adaptor hood mounted on the adaptor of FIGS. 1 and 3 and with the luer-tapered tip of the hood received in a luer-tapered bore of a relatively small catheter connector.

Referring again to the new and novel adaptor hood 32 of the present invention as illustrated in FIGS. 1, 2, 9, 10 and 11, the hood 32 is characterized by a generally tubular body member 86 molded of a suitable plastic and which is open at both its upper end 88 and its lower end 90 (as viewed in FIGS. 1, 2, and 11). Externally, the hood 32 is larger at its upper end 88 and is then tapered inwardly with a fluted or ribbed mid-body portion 92 which terminates in a reduced-diameter lower end section 90 having a relatively small end tip 94 which is provided with a luer-taper for a reason to be discussed hereinafter. As shown in the sectional portion of FIG. 10, a bore 96 extending from the larger end 88 of the tubular body member 86 is tapered inwardly toward the smaller end 90 in conformation with the outer configuration thereof.

Figure 9:
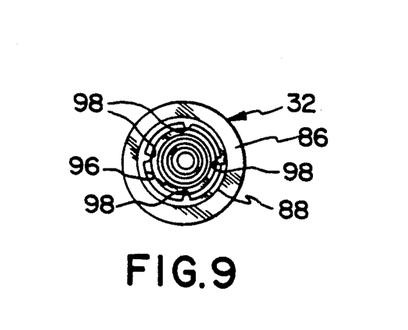
FIG. 9 is a top plan or larger end view of the adaptor hood taken generally along line 9—9 of FIG. 1.

The new and novel adaptor hood 32 may be used for either of two purposes. As illustrated in FIGS. 2 and 10, the hood 32 may be fitted over the new and novel adaptor 30 to serve as a protective shroud during storage and transport of the feeding tube set 20. As shown in FIG. 10, the larger end portion 88 grippingly fits over the largest diameter step surface 48 of the adaptor 30 and the smaller end portion 90, inwardedly of the tip 94, grippingly engages the smallest diameter step surface 54 of the adaptor 30. To improve the gripping engagement of the larger end portion 88 with the step surface 48, the bore 96 at the larger end thereof may be provided with a series of internal longitudinally extending ribs 98. For instance, four such ribs 98 are shown in FIG. 9.

The hood 32 may also be used with the adaptor 30 when the feeding tube set 20 is to be used with a "needle jejunostomy" catheter 99 having an unusually small connector 100 mounted on its proximal end, which connector 100, as illustrated in FIG. 11, has a luer-tapered bore 102 provided in its entrance end which is not designed to receive the non-luer-tapered step surface 54 of the adaptor 30. As illustrated in FIG. 11, the unique adaptor/hood combination 32, 34 is well adapted for use with catheters having such small connectors 100 provided thereon. The connector 100 is provided with a cap 104 on a flexible arm 106 for closing off the entrance end 102 thereof prior to and after a nutrient feeding operation. By lengthening the arm 106, the cap 104 could be interlocked in the locking ring 58.

Industrial Applicability

The various combinations of the improved medical devices disclosed herein improve the administration of fluid nutrients to patients including the added reliability of interlocked adaptors and Y-connectors. The use of a single universal adaptor with connectors of various sizes also contributes to further economies in the health care industry.

While there has been shown and described preferred embodiments of the invention, it would be obvious to those skilled in the art that changes and modifications may be made without departing from the invention, and it is intended by the appended claims to cover all such changes and modifications as fall within the true spirit and scope of the invention.

What is claimed as new and desired to be secured by Letters Patent of the United States is:

1. For use in various combinations between a feeding tube set and a catheter; an adaptor, a connector, and an adaptor hood;

said adaptor comprising a first generally tubular member having an upper end adapted to be mounted on the distal end of a feeding tube and a lower end adapted to be inserted into the upper end of either said connector or into said adaptor hood, the outer surface of said adaptor being characterized by a series of steps of progressively smaller diameters from the upper to the lower end thereof and including at least one inverted, slightly conical section, and a ring member projecting radially from said upper end of said first tubular member in a longitudinal plane and adapted to have a locking plug of said connector removably secured therein;

said connector comprising a second generally tubular member mounted on the proximal end of a catheter and having an open end with any one of a plurality of inner diameters and adapted to receive therein the stepped lower end of said adaptor, a locking plug projecting radially from the upper portion of said second tubular member on a flexible, resilient arm with said plug being adapted either for plugging said open upper end of said second tubular member when no adaptor is received therein or for being lockingly engaged in said adaptor ring member when said adaptor is received in said open upper end of said connector to prevent inadvertent separation of said adaptor and said connector; and said adaptor hood comprising a third generally tubular member having an open upper end, an inner bore which tapers inwardly in a downward direction, and a tip at its lower end with the outer surface thereof being provided with a luer taper for interfitting engagement thereof in the open upper end of a connector having a bore with a luer taper, which connector is mounted on the proximal end of a catheter.

2. For use in combination between a feeding tube set and a catheter; an adaptor and a connector;

said adaptor comprising a first generally tubular member having an upper end adapted to be mounted on the distal end of a feeding tube and a lower end adapted to be inserted into the upper end of said connector, the outer surface of said adaptor being characterized by a series of steps of progressively smaller diameters from the upper to the lower end thereof and including at least one inverted, slightly conical section, and a ring member projecting radially from said upper end of said first tubular member in a longitudinal plane and adapted to have a locking plug of said connector removable secured therein; and said connector comprising a second generally tubular member mounted on the proximal end of a catheter and having an open end with any one of a plurality of inner diameters and adapted to receive therein the stepped lower end of said adaptor, a locking plug projecting radially from the upper portion of said tubular member of a flexible, resilient arm with second said plug being adapted either for plugging said open upper end of said second tubular member when no adaptor is received in said open upper end of said connector or to prevent inadvertent separation of said adaptor and said connector when said plug is secured within said ring member.

3. For use in combination between a feeding tube set and a catheter; an adaptor and an adaptor hood;

said adaptor comprising a first generally tubular member having an upper end adapted to be mounted on the distal end of a feeding tube and a lower end adapted to be inserted into said adaptor hood, the outer surface of said adaptor being characterized by a series of steps of progressively smaller diameters from the upper to the lower end thereof and including at least one inverted, slightly conical section, and a ring member projecting radially from said upper end of said first tubular member in a longitudinal plane; and said adaptor hood comprising a second generally tubular member having an open upper end, and inner bore which tapers inwardly in a downward direction, and a tip at its lower end with the outer surface thereof being provided with a luer taper, said second tubular member being adapted to be fitted over said first tubular member from the lower end thereof for either providing a protective cover for said adaptor during transport or storage thereof or for providing interfitting engagement thereof in the open upper end of a connector mounted on the proximal end of a catheter, which open upper end is characterized by a bore having a luer taper.

4. For use in combination between a feeding tube set and a catheter; and adaptor, an adaptor hood, and a connector;

said adaptor comprising a first generally tubular member having an upper end adapted to be mounted on the distal end of a feeding tube and a lower end adapted to be inserted into said adaptor hood, the outer surface of said adaptor being characterized by a series of steps of progressively smaller diameters from the upper to the lower end thereof and including at least one inverted, slightly conical section;

said adaptor hood comprising a second generally tubular member having an open upper end, an inner bore which tapers inwardly in a downward direction, and a tip at its lower end with the outer surface thereof being provided with a luer taper for providing interfitting engagement thereof in the open upper end of a connector mounted on the proximal end of a catheter, which open upper end is characterized by a bore having a luer taper;

said second tubular member being adapted to be removably fitted over said first tubular member, and releasable positive interlocking means are provided between said adaptor and said connector.

5. For use between a feeding tube set and a catheter connector; an adaptor comprising a generally tubular member having an upper end adapted to be mounted on the distal end of a feeding tube and a lower end adapted to be inserted into the upper end of said catheter connector, an outer surface of said adaptor being characterized by a series of steps of progressively smaller diameters from the upper to the lower end thereof, and a locking ring member projecting radially from said upper end of said tubular member for interlocking engagement by a locking plug on said catheter connector, said locking ring member being integral with said tubular member and oriented such that the axis of said ring member is substantially perpendicular to the axis of the tubular member.

6. For use with an adaptor of a feeding tube set; an adaptor hood comprising a generally tubular member having a open upper end, a through bore which tapers inwardly in a downward direction from said upper end, said upper end being provided with several longitudinally extending internal ribs which aid the adaptor hood in gripping an outer surface of said adaptor, and said adaptor hood having a tip at its lower end with the outer surface thereof being provided with a luer taper, said tubular member being adapted to fit over a tubular adaptor of a feeding tube set from the lower end thereof for either providing a protective cover for said adaptor during transport or storage of the feeding tube set or for interfitting engagement thereof in the open upper end of a catheter connector having a bore with a luer taper.

7. For use between a feeding tube and a catheter, a positive interlock comprising a generally tubular connector mounted at the proximal end of a catheter and having an adaptor-receiving entrance port provided at its other end; a generally tubular adaptor having one end mounted on the distal end of a feeding tube and its other end insertable into said adaptor-receiving entrance port of said connector; a ring formation on said adaptor; and a plug member secured to said connector by a flexible arm and releasably engageable through said adaptor ring formation.

8. The interlock of claim 7 wherein said plug member is provided with a compressible annular ring for locking engagement with said adaptor ring formation.

9. The interlock of claim 7 wherein the outer surface of said adaptor is provided with a series of stepped surfaces of progressively smaller diameters from said one end thereof to said other end thereof, said outer surface configuration enabling insertion of said other end of said adaptor into adaptor-receiving ports of various sizes whereby said adaptor may be universally used with catheter connectors of many different sizes.

10. The interlock of claim 9 wherein said outer surface configuration of said adaptor has one or more inverted conical sections dispersed between adjacent stepped surfaces.

11. For use between a feeding tube and a catheter, improved medical devices comprising a tubular adaptor mountable on the distal end of a feeding tube and having progressively smaller diameter stepped surfaces on the outer surface thereof from the feeding tube end thereof to the opposite end thereof a tubular connector mountable on the proximal end of a catheter and having at the opposite end thereof an adaptor-receiving port of any one of several diameters, any one of which ports will insertably receive said adaptor, releasable positive interlock means engageable between said adaptor and said connector when same are assembled together, and a tubular hood having a tip with a luer taper and fittable over said adaptor to serve either as a protective shroud or as a supplemental adaptor for use with connectors wherein said adaptor-receiving port thereof is provided with an internal luer taper.

12. The improved medical devices of claim 11 wherein said interlock means comprises a ring formation provided on said adaptor and a plug formation secured to said connector by a flexible arm, said plug formation being releasably engageable in said adaptor ring formation.

13. The improved medical devices of claim 12 wherein the outer surface configuration of said tubular adaptor includes an inverted conical section.

14. The improved medical devices of claim 11 wherein the outer surface configuration of said tubular adaptor includes an inverted conical section.

* * * * *

UNITED STATES PATENT AND TRADEMARK OFFICE
CERTIFICATE OF CORRECTION

PATENT NO. : 5,057,093

DATED : October 15, 1991

INVENTOR(S) : R. Clegg, R. Coules, K. Iversen, R. Osborne, P. Schneider

It is certified that error appears in the above-identified patent and that said Letters Patent is hereby corrected as shown below:

Column 8, Line 66, "of" should be --on--

Signed and Sealed this

Sixteenth Day of March, 1993

*Attest:*

STEPHEN G. KUNIN

*Attesting Officer*     *Acting Commissioner of Patents and Trademarks*